(12) United States Patent
Millefanti et al.

(10) Patent No.: US 8,802,899 B2
(45) Date of Patent: Aug. 12, 2014

(54) METHOD FOR MANUFACTURING PERFLUOROVINYLETHERS

(75) Inventors: Stefano Millefanti, Como (IT); Vito Tortelli, Milan (IT); Giuseppe Marchionni, Milan (IT)

(73) Assignee: Solvay Specialty Polymers Italy S.p.A., Bollate (Milano) (IT)

( * ) Notice: Subject to any disclaimer, the term of this patent is extended or adjusted under 35 U.S.C. 154(b) by 375 days.

(21) Appl. No.: 12/996,351

(22) PCT Filed: Jun. 4, 2009

(86) PCT No.: PCT/EP2009/056858
§ 371 (c)(1),
(2), (4) Date: Dec. 3, 2010

(87) PCT Pub. No.: WO2009/150091
PCT Pub. Date: Dec. 17, 2009

(65) Prior Publication Data
US 2011/0098512 A1    Apr. 28, 2011

(30) Foreign Application Priority Data
Jun. 9, 2008   (EP) .................... 08157833

(51) Int. Cl.
C07C 41/24    (2006.01)
C07C 43/17    (2006.01)
(52) U.S. Cl.
USPC ........................................ 568/685; 549/455
(58) Field of Classification Search
CPC ........ C07C 41/24; C07C 43/17; C07C 317/16
USPC .......................................... 568/685; 549/455
See application file for complete search history.

(56) References Cited

U.S. PATENT DOCUMENTS

| | | | |
|---|---|---|---|
| 2,685,606 | A | 8/1954 | Clark |
| 5,068,473 | A | 11/1991 | Kellner et al. |
| 5,300,712 | A | 4/1994 | Baker |
| 5,498,806 | A | 3/1996 | Ichikawa et al. |
| 6,300,526 | B1 | 10/2001 | Navarrini et al. |
| 6,936,722 | B2 | 8/2005 | Fontana et al. |
| 7,019,177 | B2 | 3/2006 | Tortelli et al. |
| 7,319,173 | B2 | 1/2008 | Tortelli et al. |
| 2004/0267034 | A1 | 12/2004 | Anderson et al. |
| 2005/0171388 | A1 | 8/2005 | Tortelli et al. |
| 2007/0149827 | A1 | 6/2007 | Tortelli et al. |
| 2007/0203368 | A1 | 8/2007 | Tortelli et al. |

FOREIGN PATENT DOCUMENTS

| | | |
|---|---|---|
| EP | 1566374 A1 | 8/2005 |
| GB | 698386 A | 10/1953 |
| WO | WO 9008748 A1 | 8/1990 |
| WO | WO 9719751 A1 | 6/1997 |
| WO | WO 9744303 A1 | 11/1997 |

OTHER PUBLICATIONS

Mori, Tohru et al.—"Hydrodechlorination of 1,1,2-trichloro-1,2,2-trifluoroethane (CFC-113) over supported ruthenium and other noble metal catalysts", Catalysis Today, 2004, vol. 88, p. 111-120, Elsevier; 10 pgs.
Ohnishi, Ryuichiro et al.—"Selective hydrodechlorination of CFC-113 on Bi- and Tl-modified palladium catalysts", Applied Catalysis A: General, 1994, vol. 113, p. 29-41, Elsevier Science; 13 pgs.
Durrell, W.S. et al.—"Polymers of Fluorocarbon Ethers and Sulfides. I. Trifluoromethyl Trifluorovinyl Ether and Sulfide", Journal of Polymer Science: Part A, 1965, vol. 3, p. 4065-4074—XP009110173; 10 pgs.
Haszeldine, R.N. et al.—"Perfluoroalkyl Derivatives of Nitrogen. Part XXVI. The Preparation and Rearrangement of Polyfluorovinylamines and of Trifluoromethyl Trifluorovinyl Ether", J. Chem. Soc., 1968, p. 398-405—XP009097336; 8 pgs.
Okazaki, S. et al., "Hydrodechlorination of CCl$_2$FCClF$_2$ over NiO—Cr$_2$O$_3$ catalysts", Journal of Fluorine Chemistry, 1992, vol. 57, p. 191-201, Elsevier Sequoia; 11 pgs.

*Primary Examiner* — Rosalynd Keys
(74) *Attorney, Agent, or Firm* — Arent Fox LLP

(57) ABSTRACT

A process for the manufacture of a perfluorovinylether by hydrodehalogenation of a halofluoroether (HFE) having general formula (I-A) or (I-B):

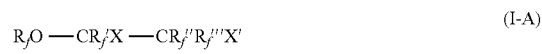

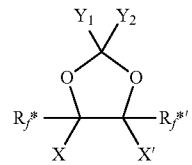

wherein $R_f$ represents a $C_1$-$C_6$ perfluoro(oxy)alkyl group; $R_f'$, $R_f''$ and $R_f'''$, equal to or different from each other, independently represent fluorine atoms or $C_1$-$C_5$ perfluoro(oxy)alkyl groups; X and X', equal to or different from each other, are independently chosen among Cl, Br or I; $R_f^*$ and $R_f^{*'}$, equal to or different from each other, independently represent fluorine atoms or $C_1$-$C_3$ perfluoro(oxy)alkyl groups; $Y_1$ and $Y_2$, equal to or different from each other, independently represent fluorine atoms or $C_1$-$C_3$ perfluoroalkyl groups. The process comprises contacting the halofluoroether (HFE) with hydrogen in the presence of a catalyst comprising at least one transition metal of group VIII B at a temperature of at most 340° C.

17 Claims, No Drawings

METHOD FOR MANUFACTURING PERFLUOROVINYLETHERS

CROSS-REFERENCE TO RELATED APPLICATIONS

The present patent application is a U.S. national stage application under 35 U.S.C. §371 of International Application No. PCT/EP2009/056858, filed Jun. 4, 2009, which claims the benefit of the European patent application No. 08157833.8, filed on Jun. 9, 2008, the whole content of this application being incorporated herein by reference for all purposes.

TECHNICAL FIELD

The present invention relates to a process for the hydrodehalogenation of halofluoroethers to perfluorovinylethers.

BACKGROUND ART

Perfluorovinylethers are useful monomers for the manufacture of various fluoropolymers, in particular thermoprocessable tetrafluoroethylene (TFE)-based plastics and elastomers.

Methods for manufacturing perfluorovinylethers are known in the art; said methods generally involve dehalogenation of suitable halofluoroether precursors in liquid phase in the presence of transition metals.

Thus, US 2007203368 (SOLVAY SOLEXIS SPA) 30.08.2007 discloses a liquid-phase process for the manufacture of perfluorovinylethers by dehalogenation of certain halofluoroethers in the presence of transition metals as zinc, copper, manganese or metal couples as Zn/Cu, Zn/Sn, Zn/Hg.

Nevertheless, processes of the prior art generally suffer from the disadvantage that significant amounts of metal halides aqueous solutions or muds are typically obtained as by-products (e.g. $ZnCl_2$ solutions/muds are produced when a chlorofluoroether is dechlorinated over zinc). Separation of said by-products from target perfluorovinylethers and their handling and disposal are time-consuming, costly and very burdensome from an industrial point of view, as these muds are highly corrosive and possibly endowed with negative environmental impact.

Need was therefore felt in the art for a cost-effective industrial process for the manufacture of perfluorovinylethers overcoming the drawbacks of liquid phase processes of the prior art.

Catalytic hydrodechlorination of chlorofluorocarbons (CFCs) to selectively yield unsaturated compounds is known in the art. GB 698386 (UNION CARBIDE) 14.10.1953 and U.S. Pat. No. 2,685,606 (UNION CARBIDE) 03.08.1954 disclose gas-phase hydrodechlorination of CFC-113 to yield 1-chloro-1,2,2-trifluoroethylene (CTFE) over supported nickel catalysts at temperatures in the range from 400 to 475° C., catalytic performances being worse at lower temperatures.

Further, catalytic hydrodechlorination of CFCs to yield unsaturated compounds at relatively low temperatures is also known in the art. U.S. Pat. No. 5,068,473 (DU PONT DE NEMOURS) 26.11.1991 discloses selective gas-phase hydrodechlorination of CFC-113 to CTFE over 5 wt. % Re/C catalyst at 200° C. Also, MORI, Tohru, et al. Hydrodechlorination of 1,1,2-trichloro-1,2,2-trifluoroethane (CFC-113) over supported ruthenium and other noble metal catalysts. *Catalysis Today*. 2004, vol. 88, p. 111-120. discloses Ru-catalyzed gas-phase hydrodechlorination of CFC-113 to yield CTFE. Very high hydrogen/substrate molar ratios are taught as mandatory for obtaining selectively unsaturated compounds, this high hydrogen consumption making the process uneconomical.

Finally, OHNISHI, Ryuichiro, et al. Selective hydrodechlorination of CFC-113 on Bi- and Tl-modified palladium catalysts. *Applied Catalysis A: General* 1994, vol. 113, p. 29-41. discloses selective gas-phase hydrodechlorination of CFC-113 to yield CTFE or 1,2,2-trifluoroethylene (TrFE) over palladium catalysts containing metal additives like, notably, Thallium at 200° C. U.S. Pat. No. 5,498,806 (DAIKIN INDUSTRIES) 12.03.1996 discloses gas-phase hydrodechlorination of CFC-113 to yield CTFE selectively over a Tl/Ru catalyst (Tl/Ru molar ratio is 2:1) at 200° C. These documents teach that using certain metal dopants, like, notably, the highly toxic Tl, it is possible to selectively promote hydrodechlorination while suppressing hydrogenation activity of said catalysts.

Now the Applicant has surprisingly found that under certain conditions the catalytic hydrodehalogenation process can be advantageously applied to halofluoroethers to obtain perfluorovinylethers with high selectivity.

DISCLOSURE OF INVENTION

It is thus an object of the present invention a process for the manufacture of a perfluorovinylether by hydrodehalogenation of a halofluoroether (HFE) having general formula (I-A) or (I-B):

(I-A)

wherein $R_f$ represents a $C_1$-$C_6$ perfluoro(oxy)alkyl group; $R_f'$, $R_f''$ and $R_f'''$, equal or different from each other, independently represent fluorine atoms or $C_1$-$C_5$ perfluoro(oxy)alkyl groups; X and X', equal or different from each other, are independently chosen among Cl, Br or I;

(I-B)

wherein $R_f^*$ and $R_f^{*'}$, equal or different from each other, independently represent fluorine atoms or $C_1$-$C_3$ perfluoro(oxy)alkyl groups; $Y_1$ and $Y_2$, equal or different from each other, independently represent fluorine atoms or $C_1$-$C_3$ perfluoroalkyl groups; X and X' are as above defined; said process comprising contacting said halofluoroether (HFE) with hydrogen in the presence of a catalyst comprising at least one transition metal of group VIII B at a temperature of at most 340° C.

The Applicant has found that by means of the process of the invention it is advantageously possible to successfully isolate perfluorovinylethers with high selectivities (exceeding 96%), with substantially no formation of metal halides-containing wastewaters and/or muds.

The process of the present invention enables advantageously selectively obtaining perfluorovinylethers of formulae respectively (A*) and (B*):

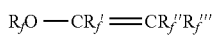 (A*)

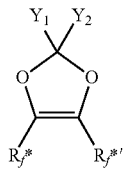 (B*)

wherein $R_f$, $R_f'$, $R_f''$, $R_f'''$, $Y_1$, $Y_2$, $R_f^*$ and $R_f^{*'}$ have same meanings as above defined,
with no need of using metal dopants, like, notably, mercury, thallium, lead, cadmium, that are known to suppress competitive-parallel hydrogenation activity of certain group VIII B transition metal catalysts, so that toxicological issues related to the use of said metal dopants are completely avoided.

As the process is carried out at temperatures not exceeding 340° C., poisoning from HF, sintering or coking phenomena otherwise known as significantly reducing group VIII B transition metal catalysts life can be essentially avoided.

The term "hydrodehalogenation", as used therein, is intended to denote the selective elimination of two halogen atoms chosen among Cl, Br or I from two adjacent fluorine-substituted carbon atoms of said halofluoroether (HFE), X, X' in formulae (I-A) an (I-B) in the presence of hydrogen, to yield the corresponding perfluorovinylether.

According to a first embodiment of the invention, the halofluoroether (HFE) of the invention is a chlorofluoroether (HFE-1) having general formula (I-A) as described above, wherein X and X', equal or different from each other, are independently chosen among Cl, Br or I, with the proviso that at least one of X and X' in said formula (I-A) is a chlorine atom.

The halofluoroether (HFE) of this first embodiment is preferably a chlorofluororoether (HFE-2) having general formula (I-A) as described above, wherein X and X' are equal to each other and are chlorine atoms, that is to say that chlorofluoroether (HFE-2) complies with formula (II-A) here below:

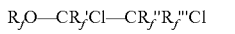 (II-A)

wherein:
$R_f$ represents a $C_1$-$C_6$ perfluoro(oxy)alkyl group, preferably a $C_1$-$C_4$ perfluoroalkyl group, more preferably a $C_1$-$C_3$ perfluoroalkyl group; $R_f'$, $R_f''$ and $R_f'''$, equal or different from each other, independently represent fluorine atoms or $C_1$-$C_5$ perfluoro(oxy)alkyl groups, preferably fluorine atoms or $C_1$-$C_3$ perfluoroalkyl groups, more preferably fluorine atoms or $C_1$-$C_2$ perfluoroalkyl groups, even more preferably fluorine atoms.

The chlorofluoroether (HFE-2) of the present invention is typically a gaseous compound under process conditions.

Representative compounds of chlorofluoroethers (HFE-2) described by formula (II-A) useful in the present invention include, but are not limited to, the following compounds:
$CF_3OCFClCF_2Cl$, $CF_3CF_2OCFClCF_2Cl$,
$CF_3CF_2CF_2OCFClCF_2Cl$, $CF_3OCF_2OCFClCF_2Cl$,
$CF_3CF_2OCF_2OCFClCF_2Cl$,
$CF_3OCF_2CF_2OCF_2OCFClCF_2Cl$.

According to a second embodiment of the invention, the halofluoroether (HFE) of the invention is a chlorofluorodioxolane (HFE-3) having general formula (I-B) as described above, wherein X and X', equal or different from each other, are independently chosen among Cl, Br or I, with the proviso that at least one of X and X' in said formula (I-B) is a chlorine atom.

The halofluoroether (HFE) of this second embodiment is preferably a chlorofluorodioxolane (HFE-4) having general formula (I-B) as described above, wherein X and X' are equal to each other and are chlorine atoms, that is to say that chlorofluorodioxolane (HFE-4) complies with formula (II-B) here below:

 (II-B)

wherein $R_f^*$ and $R_f^{*'}$, equal or different from each other, independently represent fluorine atoms or $C_1$-$C_3$ perfluoro(oxy)alkyl groups, preferably fluorine atoms or $C_1$-$C_3$ perfluorooxyalkyl groups, more preferably fluorine atoms or —$OCF_3$ groups; $Y_1$ and $Y_2$, equal or different from each other, independently represent fluorine atoms or $C_1$-$C_3$ perfluoroalkyl groups, preferably fluorine atoms.

The chlorofluorodioxolane (HFE-4) of the present invention is typically a gaseous compound under process conditions.

Representative compounds of chlorofluorodioxolanes (HFE-4) described by formula (II-B) useful in the present invention include, but are not limited to, the following compounds:

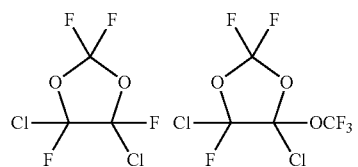

The process of the present invention is carried out in the presence of a catalyst comprising at least one transition metal of group VIII B.

For the avoidance of doubt, the term "transition metal of group VIII B" is hereby intended to denote the following metals: Fe, Ru, Os, Co, Rh, Ir, Ni, Pd, Pt.

Among preferred group VIII B transition metals, mention can be made of Ru, Ni, Pd and Pt.

The catalyst of the invention typically is a supported catalyst, that is to say that it comprises the group VIII B transition metal as above described and an inert carrier.

The inert carrier is generally selected from carbon, silica and alumina, preferably from carbon, more preferably from carbon having a BET surface area of from 800 to 1500 m$^2$/g, preferably from 1000 to 1500 m$^2$/g, even more preferably from 1100 to 1300 m$^2$/g.

The BET surface area is measured by $N_2$ adsorption as per the Brunauer, Emmett and Teller method of calculation, according to ISO 9277.

The catalyst may advantageously comprise the group VIII B transition metal in an amount of from 0.1 wt. % to 2 wt. %, preferably from 0.3 wt. % to 1.8 wt. %, more preferably from 0.5 wt. % to 1.5 wt. %.

Catalysts used in the present invention are generally activated before being used in the process of the invention by pre-reduction under hydrogen at temperatures comprised between 250° C. and 450° C., more preferably between 250° C. and 400° C., even more preferably between 300° C. and 400° C. Typically, regeneration of said catalysts is also carried out under hydrogen at temperatures comprised between 300° C. and 500° C., more preferably between 350° C. and 500° C., even more preferably between 400° C. and 500° C.

Good results have been obtained with nickel catalysts supported on carbon, wherein the amount of nickel ranges from 0.5 wt. % to 1.5 wt. %.

Very good results have been obtained with ruthenium catalysts supported on carbon, wherein the amount of ruthenium ranges from 0.5 wt. % to 1.5 wt %. It has been found that Ru/C catalysts are particularly preferred in view of their good catalytic performances at comparatively lower temperatures with respect to other supported catalysts based on group VIII B transition metals.

The process of the present invention should be carried out at a temperature of at most 340° C.

The Applicant has surprisingly found that it is essential for obtaining perfluorovinylethers in high yields to carry out the process at temperatures not exceeding 340° C. When temperature exceeds 340° C., then a dramatic drop of selectivity is observed.

Lower limits of temperatures suitable for achieving efficient conversion of halofluoroethers to perfluorovinylethers are not particularly limited. Temperatures of advantageously at least 190° C., preferably at least 200° C., more preferably at least 210° C. are generally used. Best results have been obtained 210° C. and 320° C.

The process of the present invention is advantageously carried out in gas-phase, that is to say in conditions wherein hydrogen and both the halofluoroether (HFE) and corresponding perfluorovinylether are in gaseous state. It is nevertheless understood that catalyst is generally used as a solid, so that reaction advantageously takes place between reactants in the gas phase and catalyst in the solid state.

Hydrogen can be fed either as neat reactant or diluted with an inert gas, e.g. nitrogen, helium or argon.

The process of the invention is typically carried out in any suitable reactor, including fixed and fluidized bed reactors. The process is generally carried out in continuous in a plug flow reactor comprising a fixed bed of catalyst.

Pressure is not critical. The reaction of the present invention is typically carried out under atmospheric pressure, even though pressures between 1 and 3 bar can be employed.

Contact time between the halofluoroether (HFE) and the catalyst is not particularly limited and will be chosen by the skilled in the art in relation, notably, with reaction temperature and other process parameters. Contact time, which, for continuous processes, is defined as the ratio of the catalyst bed volume to the gas flow rate in standard conditions at 0° C. and 1 bar, may vary between a few seconds and several hours; nevertheless, it is understood that this contact time is generally comprised between 2 and 200 seconds, preferably between 5 and 150 seconds.

For continuously operated process, time on stream may vary between 5 and 500 hours, preferably between 10 and 200 hours. For the avoidance of doubt, the time on stream is hereby defined as duration of continuous operations between successive reactor shut down for catalyst regeneration. It is also understood that spent catalyst can be advantageously regenerated as above mentioned and recycled in a further time on stream in the process of the invention.

Good conversions are generally obtained in the presence of a hydrogen/halofluoroether (HFE) molar ratio comprised between 0.8 and 4, preferably between 0.8 and 3, more preferably between 0.8 and 2.

It has been found that conversions typically increase by increasing the hydrogen/halofluoroether (HFE) molar ratio up to 4, a hydrogen/halofluoroether (HFE) molar ratio of larger than 4 not providing additional increase and being usually uneconomical.

A halogenidric acid is generally obtained as a by-product from the process of the invention. When the halofluoroether (HFE) is selected from a chlorofluoroether (HFE-1), a chlorofluoroether (HFE-2), a chlorofluorodioxolane (HFE-3) or a chlorofluorodioxolane (HFE-4), hydrogen chloride is typically obtained; halogenidric acids can be easily recovered by neutralization in an aqueous alkaline solution or by absorption in water.

The invention will be now described in more detail with reference to the following examples whose purpose is merely illustrative and not limitative of the scope of the invention.

GENERAL PROCEDURE

A continuous gas-phase catalytic process was carried out at atmospheric pressure in a plug-flow reactor. The overall reaction is illustrated by the following equation:

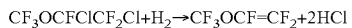

$$CF_3OCFClCF_2Cl + H_2 \rightarrow CF_3OCF=CF_2 + 2HCl$$

A predefined amount of a catalyst comprising a transition metal of group VIII B supported on carbon having a BET surface area of 1200 m²/g was loaded in a stainless steel tubular reactor having a length of 520 mm and an internal diameter of 10 mm. The catalyst bed was placed in the middle section of the reactor whereas the upper and lower sections thereof were filled with granular quartz. The catalyst was dried at 350° C. in flowing helium (5 Nl/h) during 8 hours and then cooled down to room temperature. The catalyst was then pre-reduced under a flow of hydrogen diluted with helium (5 vol. % $H_2$) while being heated at a rate of 5° C./min to 350° C. The flow of hydrogen was then increased to 10 vol. % and, after 30 minutes, a flow of hydrogen at 50 vol. % was fed during 4 hours. Once catalyst activation completed, $CF_3OCFClCF_2Cl$ and a mixture of hydrogen and helium were continuously fed into the reaction.

The gaseous reactor mixture from the reaction was sampled and analyzed by GC and GC-MS for determining selectivity and conversion.

The results are summarized here below in Table 1 (Examples 1-3). It has been found that Ru/C catalysts gave best compromise between conversions and selectivities at comparatively lower temperatures with respect to other supported group VIII B transition metal catalysts under comparatively lower flow rates of halofluoroether (HFE) reactant.

Comparative examples 1C and 2C were also run in the presence of supported group VIII B transition metal catalysts showing that selectivity was found to dramatically drop at temperatures exceeding 340° C.

TABLE 1 (*)

| Example | Catalyst | Catalyst amount (g) | T (° C.) | WHSV (§) | Conversion (%) | Selectivity (%) |
|---|---|---|---|---|---|---|
| 1 | 1.5 wt. % Ni/C | 2.6 | 310 | 2.0 | 14.9 | 96.5 |
| 2 | 1.0 wt. % Ru/C | 3.5 | 220 | 1.3 | 20.6 | 97.6 |

TABLE 1 (*)-continued

| Example | Catalyst | Catalyst amount (g) | T (° C.) | WHSV (§) | Conversion (%) | Selectivity (%) |
|---|---|---|---|---|---|---|
| 3 | 1.0 wt. % Ru/C | 3.5 | 280 | 1.3 | 20.3 | 98.5 |
| 1C | 1.5 wt. % Ni/C | 2.8 | 350 | 2.2 | 4.7 | 78.7 |
| 2C | 1.0 wt. % Ru/C | 3.6 | 350 | 1.4 | 27.2 | 65.4 |

(*) $H_2/CF_3OCFClCF_2Cl$ molar ratio: 1.0; time on stream: 20 h;
(§) weight hourly space velocity ($g_{ether}/h/g_{catalyst}$).

Further, Table 2 here below summarizes experimental data obtained for a selection of supported group VIII B transition metal catalysts by increasing the hydrogen/$CF_3OCFClCF_2Cl$ molar ratio. As well shown in examples 4-6, at given temperature and catalyst loading, conversion can be advantageously increased by increasing the hydrogen/halofluoroether (HFE) molar ratio, with no detrimental impact on selectivity.

TABLE 2 (**)

| Example | $H_2/CF_3OCFClCF_2Cl$ Molar ratio | WHSV (§) | Conversion (%) | Selectivity (%) |
|---|---|---|---|---|
| 4 | 0.8 | 3.0 | 15.0 | 97.7 |
| 5 | 1.0 | 3.0 | 23.4 | 97.4 |
| 6 | 2.0 | 3.0 | 73.1 | 97.2 |

(**) Catalyst: 1.0 wt. % Ru/C;
catalyst amount: 3.5 g;
reaction temperature: 250° C.;
time on stream: 10 h;
(§) weight hourly space velocity ($g_{ether}/h/g_{catalyst}$).

As shown in Table 3 here below (Examples 7-9), at given hydrogen/halofluoroether (HFE) molar ratio, good selectivities are advantageously obtained even at comparatively lower catalyst loading.

TABLE 3 (***)

| Example | Catalyst | WHSV (§) | Conversion (%) | Selectivity (%) |
|---|---|---|---|---|
| 7 | 0.5 wt. % Ru/C | 3.0 | 23.2 | 97.4 |
| 8 | 1.0 wt. % Ru/C | 3.0 | 23.4 | 97.4 |
| 9 | 1.5 wt. % Ru/C | 3.0 | 21.8 | 97.0 |

(***) Catalyst amount: 3.5 g;
$H_2/CF_3OCFClCF_2Cl$ molar ratio: 1.0;
reaction temperature: 250° C.;
time on stream: 10 h;
(§) weight hourly space velocity ($g_{ether}/h/g_{catalyst}$).

The invention claimed is:

1. A process for the manufacture of a perfluorovinylether by hydrodehalogenation of a halofluoroether (HFE) having general formula (I-A) or (I-B):

$$R_fO—CR_f'X—CR_f''R_f'''X' \quad (I-A)$$

wherein $R_f$ represents a $C_1$-$C_6$ perfluoro(oxy)alkyl group; $R_f'$, $R_f''$ and $R_f'''$, equal to or different from each other, independently represent fluorine atoms or $C_1$-$C_5$ perfluoro(oxy)alkyl groups; X and X', equal to or different from each other, are independently selected from the group consisting of Cl, Br, and I;

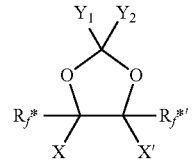

(I-B)

wherein $R_f^*$ and $R_f^{*'}$, equal to or different from each other, independently represent fluorine atoms or $C_1$-$C_3$ perfluoro(oxy)alkyl groups;
Y$_1$ and Y$_2$, equal to or different from each other, independently represent fluorine atoms or $C_1$-$C_3$ perfluoroalkyl groups; X and X' are the same as for formula (I-A); said process comprising contacting said halofluoroether (HFE) with hydrogen in the presence of a catalyst comprising at least one transition metal of group VIII B at a temperature of at most 340° C.,
wherein the process is carried out in gas-phase.

2. The process of claim 1, wherein the halofluoroether (HFE) is a chlorofluoroether (HFE-1) having general formula (I-A), wherein X and X', equal to or different from each other, are independently selected from the group consisting of Cl, Br, and I, with the proviso that at least one of X and X' in said formula (I-A) is a chlorine atom.

3. The process of claim 1, wherein the halofluoroether (HFE) is a chlorofluoroether (HFE-2) having general formula (II-A):

$$R_fO—CR_f'Cl—CR_f''R_f'''Cl \quad (II-A)$$

wherein $R_f$ represents a $C_1$-$C_6$ perfluoro(oxy)alkyl group; $R_f'$, $R_f''$ and $R_f'''$, equal to or different from each other, independently represent fluorine atoms or $C_1$-$C_5$ perfluoro(oxy)alkyl groups.

4. The process of claim 1, wherein the catalyst comprises at least one transition metal of group VIII B and an inert carrier.

5. The process of claim 4, wherein the catalyst is a ruthenium catalyst supported on carbon.

6. The process of claim 5, wherein the amount of ruthenium ranges from 0.5 wt. % to 1.5 wt. %.

7. The process of claim 1, said process being carried out at a temperatures comprised between 190° C. and 340° C.

8. The process of claim 1, wherein the hydrogen/halofluoroether (HFE) molar ratio is comprised between 0.8 and 4.

9. The process of claim 3, wherein $R_f$ represents a $C_1$-$C_4$ perfluoroalkyl group.

10. The process of claim 3, wherein $R_f$ represents a $C_1$-$C_3$ perfluoroalkyl group.

11. The process of claim 3, wherein $R_f'$, $R_f''$ and $R_f'''$, equal to or different from each other, independently represent fluorine atoms or $C_1$-$C_3$ perfluoroalkyl groups.

12. The process of claim 3, wherein $R_f'$, $R_f''$ and $R_f'''$, equal to or different from each other, independently represent fluorine atoms or $C_1$-$C_2$ perfluoroalkyl groups.

13. The process of claim 3, wherein $R_f'$, $R_f''$ and $R_f'''$ represent fluorine atoms.

14. The process of claim 7, being carried out at a temperature comprised between 200° C. and 340° C.

15. The process of claim 7, being carried out at a temperature comprised between 210° C. and 320° C.

16. The process of claim 8, wherein the hydrogen/halofluoroether (HFE) molar ratio is comprised between 0.8 and 3.

17. The process of claim 8, wherein the hydrogen/halofluoroether (HFE) molar ratio is comprised between 0.8 and 2.

* * * * *